United States Patent [19]

Pavkovich et al.

[11] 4,365,339
[45] Dec. 21, 1982

[54] TOMOGRAPHIC APPARATUS AND METHOD FOR RECONSTRUCTING PLANAR SLICES FROM NON-ABSORBED AND NON-SCATTERED RADIATION

[75] Inventors: John M. Pavkovich, Palo Alto; Craig S. Nunan, Los Altos Hills, both of Calif.

[73] Assignee: General Electric Company, Milwaukee, Wis.

[21] Appl. No.: 941,506

[22] Filed: Sep. 11, 1978

Related U.S. Application Data

[62] Division of Ser. No. 643,894, Dec. 23, 1975, Pat. No. 4,149,247.

[51] Int. Cl.$^3$ .............................................. A61B 6/00
[52] U.S. Cl. .................................... 378/015; 378/16; 378/901; 364/414
[58] Field of Search ................... 250/445 T; 364/414; 378/15, 16, 901

[56] References Cited

U.S. PATENT DOCUMENTS 3,866,047 2/1975 Hounsfield ...................... 250/445 T
4,051,378 9/1977 Krippner ......................... 250/445 T Primary Examiner—Davis L. Willis
Assistant Examiner—T. N. Grigsby
Attorney, Agent, or Firm—Dana F. Bigelow; Douglas E. Stoner

[57] ABSTRACT

In a tomographic apparatus and method for reconstructing two dimensional planar slices from linear projections of non-absorbed radiation useful in the fields of medical radiology, microscopy, and non-destructive testing, a beam of radiation in the shape of a fan is passed through an object lying in the same quasi plane as the object slice and non-absorption thereof is recorded on oppositely situated detectors aligned with said source of radiation. There is relative rotation between the source-detector configuration and the object within the quasi-plane. Periodic values of the detected radiation are taken, convolved with certain functions, and back-projected to produce a two-dimensional output picture on a visual display illustrating a facsimile of the object slice. A series of two-dimensional pictures obtained simultaneously or serially can be combined to produce a three-dimensional portrayal of the entire object. The invention is the first device which uses a fan beam source of radiation coupled with the application of a convolution method of data reduction with no intervening reordering of fan beam rays, thereby eliminating errors and delays in computation time which would be involved in such reordering. The invention is the first method for providing an exact reconstruction of a two-dimensional picture of an object slice from a series of one-dimensional projections of radiation not absorbed by the slice when the superior fan beam source is employed.

1 Claim, 4 Drawing Figures

O = CENTER OF ROTATION
S = RADIATION SOURCE
P = POINT OF INTEREST IN OBJECT
R = DISTANCE FROM AXIS OF ROTATION TO S
D = DISTANCE FROM O TO P
Z = DISTANCE FROM S TO P
$= [R^2 + D^2 - 2RD \cos \theta]^{1/2}$

TOMOGRAPHIC APPARATUS AND METHOD FOR RECONSTRUCTING PLANAR SLICES FROM NON-ABSORBED AND NON-SCATTERED RADIATION

This is a division of application Ser. No. 643,894 filed Dec. 23, 1975 and now U.S. Pat. No. 4,149,247.

BACKGROUND OF THE INVENTION

1. Field of the Invention

This invention relates to a method and apparatus for constructing a two-dimensional picture of an object slice from linear projections of radiation not absorbed by the object, useful in the fields of medical radiology, microscopy, and non-destructive testing. The branch of the invention employing x-rays for medical radiology is sometimes referred to as computerized tomography.

2. Description of the Prior Art

It is useful in many technologies to construct a two-dimensional pictorial representation from a series of linear data resulting from sensory projections taken through a quasi-plane within which lies the two-dimensional planar slice of the object that one wishes to reconstruct. For example, in the case of utilizing X-rays to provide a pictorial representation of the inside of a human body it is known to pass X or gamma radiation through the tissues of the body and measure the absorption of this radiation by the various tissues. The nature of the tissues may then be determined by the percentage extent of absorption in each tissue of the radiation, since different tissues are known to absorb differing amounts of radiation.

Passing a wall of radiation through an object and detecting the amount of absorption within the object by means of complementary-spaced detectors results in a three-dimensional object being projected onto a two-dimensional picture. This can result in the superimposition of information and resulting loss of said information. More sophisticated techniques must be devised if one wishes to examine a body with greater sensitivity to spatial variations in radiation absorption and fewer superimposition effects.

In a method known as general tomography a source of radiation and a photographic film are revolved along an elliptical or other path near the body in such a way that elements in one plane of the body remain substantially stationary. This technique is utilized to obtain relevant information along a two-dimensional planar slice of the body. This method has a disadvantage in that shadows of bodily tissues on planes of the body other than the desired planar slice appear as background information partially obscuring the information desired to be obtained from the cognizant slice.

In an attempt to obtain more accurate information, methods have been proposed whereby the radiation and detection of small all lie within the planar slice of the object to be examined. A two-dimensional reconstruction of the thin slice of the object is then performed, and repeated for each slice desired to be portrayed or diagnosed.

In A. M. Cormack, "Representations of a Function by Line Integrals with Some Radiological Applications", Journal of Applied Physics, Vol. 34, No. 9, pp. 2722–2727, (September 1963), (reference 1), the author used a collimated 7 millimeter diameter beam of cobalt 60 gamma rays and a collimated Geiger counter. About 20,000 counts were integrated for each 5 millimeter lateral displacement of the beam which passed through a phantom 5 centimeters thick and 20 centimeters in diameter comprising concentric cylinders of aluminum, aluminum alloy and wood. Because of symmetry of the phantom, measurements were made at only one angle. The resulting calculated absorption coefficients were accurate to plus or minus 1.5 percent.

In October, 1964, the same author in "Representations of a Function by Line Integrals with Some Radiological Applications. II", Journal of Applied Physics, Vol. 35, No. 10, pp 2908–2913, (2), separated the two-dimensional problem into a set of one-dimensional integral equations of a function with solely radial variation. The measurements were expanded in a sine series with coefficients identical to those of the radial density function when expanded in a limited series of Zernicke polynomials. This method is mathematically equivalent to a Fourier transform technique but differs in practical application, such as significance of artifacts introduced by interpolation. Cormack used a collimated 5×5 millimeter beam of cobalt 60 gamma rays and a collimated Geiger counter. About 20,000 counts were integrated for each beam position. The beam was displaced laterally by 5 millimeter intervals to form a parallel set of 19 lines and the set was repeated at 7.5 degree intervals for 25 separate angles. The phantom was 2.5 centimeters thick, 20 centimeters in diameter, comprising an aluminum disc at the center, an aluminum ring at the periphery, an aluminum disc off axis, and the remainder Lucite. From 475 independent measurements, 243 constants were determined and used to synthesize the absorption distribution. The resulting accuracy of calculated absorption values was good on average but ringing was introduced by the sharp changes in density. Cormack's method is capable in theory of yielding a unique principal solution, but is nevertheless complicated, has limited practical application and is liable to error in its practically feasible forms.

D. J. DeRosier and A. Klug in "Reconstruction of Three-Dimensional Structures from Electron Micrographs", Nature, Vol. 217, pp. 130–134 (Jan. 13, 1968), (3), used Fourier transformation of two-dimensional electron transmission images (electron micrographs) at a number of angles (30 for nonsymmetric objects) to produce a series of sections representing the object in three dimensions. Resolution of the final three-dimensional Fourier density map was 30 Angstroms, for a 250 Angstrom T4 bacteriophage tail.

R. G. Hart, "Electron Microscopy of Unstained Biological Material: The Polytropic Montage", Science, Vol. 159, pp. 1464–1467 (March, 1968), (4), used 12 electron micrographs taken at different angles, a flying spot scanner, cathode ray tube and a CDC-3600 computer (Control Data Corporation, Minneapolis, Minn.) with 48 bit, 32K word core to produce a section display by digital superposition. Resolution approached 3 Angstroms.

D. E. Kuhl, J. Hale and W. L. Eaton, "Transmission Scanning: A Useful Adjunct to Conventional Emission Scanning for Accurately Keying Isotope Deposition to Radiographic Anatomy", Radiology, Vol. 87, pp. 278–184, in August, 1966, (5), (see FIG. 10) installed a collimated radioactive source (100 millicuries of 60 keV Americium-241) opposite one detector of a scanner which had two opposed detectors. (Kuhl also suggested that a 1 millicurie 30 keV Iodine-125 source could be installed opposite each of the detectors of a two detector sytem.) A 6.3 millimeter hole was drilled in the collimator of the opposing detector. The opposed detectors were translated together to scan the patient at each of a number of angles usually 15 degrees apart (see Kuhl and Edwards, "Cylindrical and Section Radioisotope Scanning of Liver and Brain", Radiology, Vol. 83, 926, November, 1964, at page 932) (6). A CRT (cathode ray tube) beam was swept to form a narrow illuminated line corresponding to the orientation and position of the 6.3 millimeter gamma beam through the patient and as the scan proceeded the brightness of the line on the CRT was varied according to the count rate in the detector; a transverse section image was thus built up on a film viewing the CRT. Kuhl found the transverse section transmission scan to be especially useful for an anatomic orientation of a simultaneous transverse section emission scan of the human thorax and mediastinum.

At the June, 1966 meeting of the Society of Nuclear Medicine in Philadelphia, Dr. Kuhl (D. E. Kuhl and R. Q. Edwards, Abstract A-5 "Reorganizing Transverse Section Scan Data as a Rectilinear Matrix Using Digital Processing", Journal of Nuclear Medicine, Vol. 7, P. 332, (June, 1966), (7), described the use of digital processing of his transverse section scan data to produce a rectilinear matrix image superior to the images obtained with the above method of film exposure summation of count rate modulated CRT lines. The scan data from each detector was stored on magnetic tape, comprising a series of scans at 24 different angles 7.5 degrees apart around the patient. One hundred eighty-one thousand operations were performed in 12 minutes on this data to produce a transverse section image matrix of 10,000 elements.

The process is described in more detail in D. E. Kuhl and R. Q. Edwards, "Reorganizing Data from Transverse Section Scans of the Brain Using Digital Processing", Radiology, Vol. 91, p. 975 (November, 1968) (8). The matrix comprised a 100 by 100 array of 2.5 millimeter by 2.5 millimeter elements. For each picture element the counts recorded on the scan line through the element at each of the 24 scan angles were extracted by programmed search from drum storage, summed, divided by 24 and stored on tape, after which they could be called sequentially to produce a CRT raster scan.

R. A. Crowther, D. J. DeRosier, and A. Klug, in "The Reconstruction of a Three Dimensional Structure from Projections and Its Application to Electron Microscopy", Proceedings of the Royal Society of London, 317A, 319 (1970), (9), developed a formal solution of the problem of reconstructing three-dimensional absorption distributions from two-dimensional electron micrograph projections, using Fourier transformation. They considered a series of 5 degree tilts from +45 degrees to −45 degrees and found that at least $\pi D/d$ views are required to reconstruct a body of diameter D to a resolution of d.p. 332.

M. Goitein, in "Three Dimensional Density Reconstruction from a Series of Two-Dimensional Projections", Nuclear Instruments and Methods 101, 509 (1972), (10), shows that standard matrix inversion techniques for two dimensional reconstructions require too much storage space. He states that a 50K word memory is required for an inversion of a 225×225 matrix for a 15×15 element object grid and that with use of overflow memory the execution time increases as the sixth power of the number of cells along the edge of the object grid, p. 511. He proposes an iterative relaxation procedure since an "exact solution" is not computationally accessible for a typical object grid such as 100×100 elements. This technique involves adjusting the density of any cell to fit all measurements which involve that cell, "fit" being on the basis of least-squares minimization. He used the Cormack (1964) phantom design as a model, simulated it on a computer, "measured" absorption with a scan of 51 transversely separated lines repeated at 40 uniformly spaced angles, introduced 1% random error in the measurements and computed the absorption distribution in a transverse section view on a 30×30 grid using 15 iterations. He also computed absorption distributions in transverse section view using the original absorption data recorded by Cormack (1964) as well as data furnished by others from alpha beam and X-ray beam transmission measurements.

D. Kuhl, R. Q. Edwards, A. R. Ricci and M. Reivich, in "Quantitative Section Scanning Using Orthogonal Tangent Correction", Abstract, Journal of Nuclear Medicine Vol. 13, p. 447 (June, 1972), (11), describe an iterative computation method combining the data from a scan at one angle with the data from a scan at 90 degrees to this angle, and repeating this computation process for a multitude of angles. An iterative correction is continued through all angles, requiring 10 minutes with a Varian 16 bit 8K word core computer (Varian Data Machines, Irvine, Calif.).

All of these methods suffer from certain deficiencies. The errors inherent in such prior art techniques are not easily ascertainable. The time to gather the data is slow; in the case of X-ray diagnosis, this increases the time the patient must be strapped in an uncomfortable position and limits the throughput, i.e., total patient handling capacity, of the machine. It also means that for slices of body regions such as the abdominal cavity, the patient's normal breathing produces motion in the phantom during the taking of measurements and consequent blurring of the output picture, which can mask, for example, the presence of tumors. The time required to reduce the data to picture form is lengthy, typically on the order of a quarter of an hour. Spatial resolution of the output picture is often relatively poor.

D. Boyd, J. Coonrod, J. Dehnert, D. Chu, C. Lim, B. MacDonald, and V. Perez-Mendez, "A High Pressure Xenon Proportional Chamber for X-Ray Laminographic Reconstruction Using Fan Beam Geometry," IEEE Transactions on Nuclear Science, Vol. NS-21, No. 1 (Feb. 1974) (12), describe, at P. 185, a reconstruction method for a fan beam source which employs a convolution method of data reconstruction. This use of a fan beam can result in a reduction in data-gathering time, and a more efficient utilization of radiation flux. However, the fan beam rays are first reordered into parallel beam rays, then a known parallel ray convolution method is employed. This step of first reordering the data introduces a delay. An additional problem with this method is that normal optimization of design criteria in most applications requires that the angle between individual rays of the fan beam be less than the angle of arc between pulses of the source. Thus, there is no one-to-one matchup between fan beam rays and parallel beam rays. As a result, approximations must be made during the reordering step, causing a diminution in resolution in the output picture. Even in the case where there is a one-to-one relationship between fan beam rays and parallel beam rays, the distances between the resultant parallel beam rays will be unequal. Therefore, another set of resolution-diminishing approximations must be made. Another problem with reordering is that reordering forces one to fix irrevocably the number of pulses per revolution of the source. This results in a loss of flexibility because, for example, the wider the object being pictured, the smaller the arcuate angle between pulsing required for the same resolution. If one does not reorder, one can design into the machine convenient means whereby the operator may adjust the arcuate angle between pulsing depending upon the object size.

No prior art method combines the use of a fan beam source and the application of a convolution method of data reconstruction with no intervening reordering of the detected projection profiles over each other. No prior art method is capable of providing an exact reconstruction of a two-dimensional picture from a series of one-dimensional projections when the superior fan beam source is employed.

OBJECTS OF THE INVENTION

It is therefore a primary object of the instant invention to provide an improved method and apparatus for reconstructing two-dimensional pictures from a succession of linear projections for use in computerized tomography, electron microscopy, and other fields of technology, and for creating three-dimensional pictures by piecing together a series of two-dimensional pictures.

It is a further object of the present invention to provide means for obtaining a two-dimensional X-ray pictorial representation of a slice of a human or other body in which the body is exposed to radiation for a shorter time than in the prior art.

It is another object of the instant invention to provide for more accurate two-dimensional reconstruction of an image based upon a succession of one-dimensional data obtained by projecting radiation through the object slice in its quasi-plane.

It is still another object of the instant invention to provide an improved means for reconstructing a two-dimensional pictorial representation of a planar slice of an object by passing radiation through the object, in which the errors inherent in the pictorial reconstruction are readily ascertainable.

It is another object of the instant invention to provide an improved apparatus and method for reconstructing a two-dimensional picture from a series of one-dimensional projection profiles in which the data acquisition and data reconstruction times are both substantially reduced over the prior art for the same degree of resolution.

It is another object of the instant invention to project a fan beam of radiation through an object slice in its quasi-plane and reconstruct a picture of the object by means of a convolution method of data reconstruction which operates on the detected projection profiles produced by the fan beams with no intervening reordering of fan beam rays into a different set of rays.

It is yet another object of the instant invention to provide an exact reconstruction replica of a two dimensional object slice when a fan beam of radiation is passed through the object at different angles creating a set of one dimensional measured projections.

It is another object of the instant invention to graphically picture a reconstruction of a two dimensional object based on a set of one-dimensional projection values corresponding to amounts of detected radiation non-absorbed by the object, in which the resolution is improved over the prior art for the same data acquisition and reconstruction times.

SUMMARY OF INVENTION

Briefly and in accordance with the above objects the present invention is concerned with a method and apparatus for constructing a two-dimensional picture of an object slice from linear projections obtained by passing radiation in quasi-planar form through the quasi-plane of the object slice at various angles and measuring amounts of radiation not absorbed by said object slice. By quasi-plane is meant plane-like with small but finite thickness. This method and apparatus can be used in the fields of medical radiology, microscopy, non-destructive testing, and other fields as well.

A fan beam of radiation (which may be light, heat, sound, transmissive ultrasound, electro-magnetic radiation, X-rays, gamma rays, or sub-atomic particles such as electrons, protons, neutrons, or heavy ions, or any other form of transmissive radiation) is passed through an object slice lying in a quasi-plane. The quasi-plane has a small thickness, in the case of X-ray diagnosis, typically but not necessarily between about 1 millimeter and 15 millimeters. The entire three-dimensional object can be portrayed by picturing a series of side-by-side slices each 1 to 15 mm thick. The whole series can be mapped and pictured simultaneously.

The object absorbs some of the radiation, scatters some additional radiation, and the rest is detected by an elongate detector or detectors situated opposite the source of fan radiation, and aligned therewith, lying in the same plane as the source of radiation and the object slice. The angular distance between each individual detection point is constant. Thus the detector bank is preferably arcuate in geometry, and may comprise an entire circle or ellipse; or the detector bank lies in a straight line with each individual detection point oriented toward the source. A compensator may be positioned around the object to reduce the variation in intensity of radiation reaching the detector(s). Data may be extracted from the detector(s) serially or in parallel, continuously or in pulses. In the case of gamma or X-radiation, each individual detector element may comprise a scintillator of gas, liquid, or solid employing a crystalline substance such as sodium iodide and a photo-multiplier or photodiode. Alternatively, it may comprise an ionization chamber filled with a high atomic numbered element such as xenon in gas, liquid, or solid phase, with or without a lower atomic numbered element such as argon in similar form as the xenon to capture K-emission X-rays. Alternatively, the detector may be a semiconductor such as high purity germanium or cadmium telluride or mercuric iodide, or it may be an image intensifier. The detector may operate in current integration mode or it may count individual gamma-ray or X-ray photons. The detector may comprise a scintillation screen-film combination moved perpendicular to the fan beam to record successive projection profiles at successive source angles, with a flying spot scanner extracting the data from the developed film.

The radiation beam and the detectors may be continuous but are usually discrete. In either case, the resultant detected radiation may be fed into a computer for conversion into a two-dimensional pictorial representation on a graphical display device such as a cathode ray tube (CRT) or a printed sheet of paper capable of illustrating densities or contours. If a digital computer is employed with a detector providing analog output, the information is first processed by an analog-to-digital converter. If an analog computer is employed with a detector providing digital output, the information is first processed by a digital-to-analog converter. In either case, the computer calculates the degree of absorption for each cell in a mesh or grid superimposed upon the object slice portrayed, and this data is then processed and converted into an analog or digital two-dimensional pictorial form.

In the case of using radiation to diagnose human and other animal bodies, it is possible to distinguish and vividly portray aneurysms, hemorrhages, tumors, abnormal cavities, blood clots, enlarged organs, and abnormalities in ventricles (for example) since it is known that different tissues of the body absorb differing amounts of radiation.

The instant invention is the first method and apparatus which uses a convolution reconstruction method on fan beam rays with no prior reordering of the fan beam rays into a net set of rays.

A "convolution process" of x, c(x), according to the mathematical literature, is any integral or summation function of the form:

$$c(x) = \int f(x - x')g(x')dx' \text{ or}$$

$$c(x) = \sum_n f(x - x_n)g(x_n)$$

By "convolution method" is meant any method which employs such a convolution process.

The convolution method is much faster and provides equal or better resolution for the same amount of radiation than iterative methods used in the prior art. See "The Fourier Reconstruction of a Head Section", by L. A. Shepp and B. F. Logan, Bell Laboratories, Murray Hill, New Jersey, July 1974, (13), pp. 5,7, in which a convolution method for parallel geometry (14), is favorably compared with an iterative method of successive approximations. The instant invention accentuates this favorability because it uses a direct convolution method based upon polar geometry. No wasteful and error producing prior reordering of the rays into parallel rays is required to take advantage of the superior properties of fan beams.

The instant invention is also capable of showing the relationship between the measurements taken and the errors inherent in them, since the discrete embodiment is really a special case of the continuous embodiment, and one can gauge the effect of each simplifying approximation in turn.

The advantage to the fan beam is that it permits a faster data gathering than with a parallel beam source produced by translating a source and detector, and one can obtain a large number of measurements without moving the source, thus reducing the effects of mechanical vibrations which can impair accuracy. In the case of X-radiation applied to the body of a human or other animal, the patient is forced to lie still for a much shorter period of time and more patients can be processed by the machine in a given amount of time. Significantly, since all the data required for a cross-sectional scan can be acquired in the order of one second (one to two orders of magnitude faster than existing systems) it is now possible for the first time to obtain accurate pictures of areas of the body such as the abdominal cavity, without requiring extensive periods of breath-holding by the patient and with less motion artifact due to peristalsis and other organ motion.

The source-detector array is typically rotated about the object slice in a circular path comprising 360 degrees. Alternatively, the object may rotate within a stationary source-detector assembly. Other configurations are also possible and are described below in the Detailed Description of the Preferred Embodiment. The source may be rotated continuously or step-wise in small angular steps. In either case, the radiation may emanate from the source continuously (for example, in the case where the source is radioactive), or in the form of periodic pulses or bursts. The detected data is convolved and back-projected without the necessity for first reordering the data into a new set of rays, for example, a set of parallel rays, as in prior art fan beam systems. By "back-projection" is meant the process of converting the convolved projection profile data associated with the detectors into values of absorbed density at an arbitrary number of points P preselected throughout the object slice under examination.

The instant invention encompasses the first exact reconstruction of a two-dimensional picture of an object slice from a series of one-dimensional projections of radiation non-absorbed by the slice when the superior fan beam source is employed. This means that the accuracy and resolution of the output picture are good even when data gathering and data reconstructing times are small. Thus, the fan beam approach is strengthened as a viable tool of scientific inquiry.

In addition, since an exact reconstruction is achieved, (limited only by imperfections in the instrumentation employed and intentionally introduced approximating variations to the general case), it is possible to more directly perceive the relationship between an introduced approximation and the quality and speed of the output response. Thus, a more precise control over the resolution/speed tradeoff is obtained compared with the known prior art.

BRIEF DESCRIPTION OF THE DRAWINGS

These and other more detailed and specific objects and features of the instant invention are more fully disclosed in the following specification, reference being had to the accompanying drawings in which.

DETAILED DESCRIPTION OF THE PREFERRED EMBODIMENT

Figure 1:
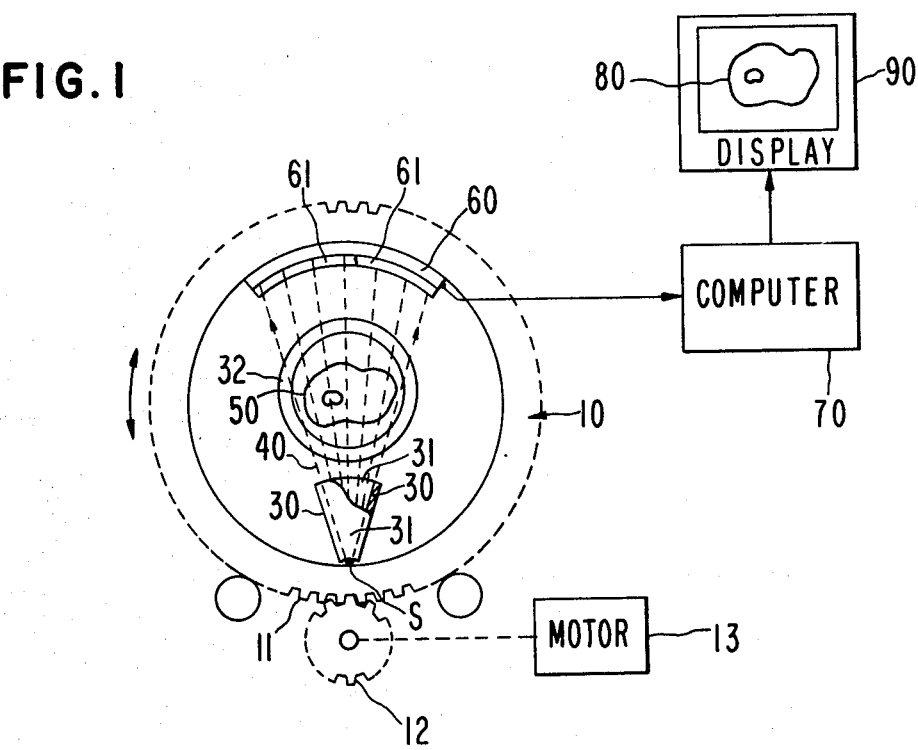
FIG. 1 is a partially schematic, partially block diagram of the embodiment of the system of the instant invention in which the data acquisition phase is continuous.

FIG. 1 shows a schematic and block diagram of the exact embodiment of the instant invention, i.e., when the data gathering is performed continuously. A source S of radiation, object slice 50, and a continuous detector 60 are lying in the same quasi-plane, which has a finite but small thickness, typically on the order of a few millimeters in the case of computerized tomography.

Source S and continuous detector 60 are aligned and are preferably constructed so as to be always opposite each other; for example, they are each fixedly mounted on gantry 10 which rotates in a circular path around object slice 50. Alternatively, the object may rotate within a motionless source-detector assembly. Alternatively, one 360 degree continuous detector could be motionlessly mounted with just the source rotating. Or, a plurality of sources may be employed each over a portion of the circle; or else, one 360 degree continuous source could be employed with energization of only one point of said source at any given time, said point traversing the entire 360 degree arc over time.

The rotational force may be provided by a motor 13 which transmits energy to gantry gears 11 by means of drive gear 12. Continuous detector 60 preferably follows source S opposite thereto, and is preferably arcuate in shape. When arcuate, its geometry is preferably such that each point on the detector is equidistant from the source S.

Source S may be any type of radiation such as an electron beam in the case of electron microscopy or X or gamma radiation for examining a human, or other body. In the case where exact data reconstruction is desired (see equation 33, infra.) the source is energized continuously throughout a complete 360 degree traversal of its circular path. Otherwise the source may pulse. In the case of X-radiation, detector 60 is typically a scintillator fabricated of a crystalline material such as sodium iodide plus a photomultiplier or photodiode; or it may comprise an ionization chamber filled with a substance such as xenon, or a mixture of substances such as xenon and argon, in gas, liquid, or solid phase; or it may comprise an emulsive film.

Collimators 30 shape the beam of radiation emanating from source S into the shape of a fan, at least as wide as object 50. Collimators 31 (parallel to the plane of the paper in FIG. 1) are spaced one beside the other to shape the fan into a thin quasi-planar beam, which does not necessarily have to be of uniform thickness; for example, if a point source of radiation is used, the beam will fan in a vertical as well as a horizontal direction. Detector collimators 61 serve to minimize the effects of Compton scatter from planes other than the imaging quasi-plane. Collimators 30, 31 and 61 are typically fabricated of lead, but may be made from any material which absorbs the radiation in unwanted directions. In the case of X-ray diagnosis the thickness of the fan, as defined by collimators 31, is typically between 1 mm and 15 mm at the middle of the object. The arc that is cut by the fan is sufficiently large to cover the entire object slice.

Compensator 32, which may be a bag filled with water or plastic, may optionally be positioned enshrouding object 50 for the purposes of attenuating certain fan beam ray intensities and thereby reducing the range of intensities over which detector 60 must be responsive. The compensator may be fixedly mounted on gantry 10 so as to rotate therewith, or it may be mounted fixedly with respect to object 50.

As the source-detector array undergoes relative rotation with respect to the object (continuously where exact reconstruction is desired) over a time of approximately one to 15 seconds, reading of absorbed radiation are time-continuously measured along detector 60. The data acquisition is preferably completed during one relative revolution (i.e., 360 degrees) of the system. Data from the detector may first be smoothed, is convolved with other data in a way which will be described below, may be smoothed again, and is then stored in computer 70 which, if analog, may comprise an analog store such as an acoustic wave or video disc. If digital, the computer is preferably a high-speed computer. The data is later back-projected with other data to produce an output picture 80 which is a replica of object 50.

The output picture is portrayed on a visual display device 90 such as a CRT (cathode ray tube) or an electrostatic output terminal which is capable of showing density of the object being portrayed as depth, contour, shadings, or color. A photograph or other hard copy of the CRT image may then be taken.

A series of two-dimensional pictures may be obtained by either taking a succession of pictures as above, or else by fabricating an array comprising a plurality of source-detector configurations spaced beside each other e.g., mounted side-by-side on gantry 10. In either case, the output may be portrayed as a three-dimensional picture, for example, by portraying each output element as a shaded or colored translucent ball or cube. Alternatively, a series of transparent light panels may be used for a three-dimensional display.

Figure 2:
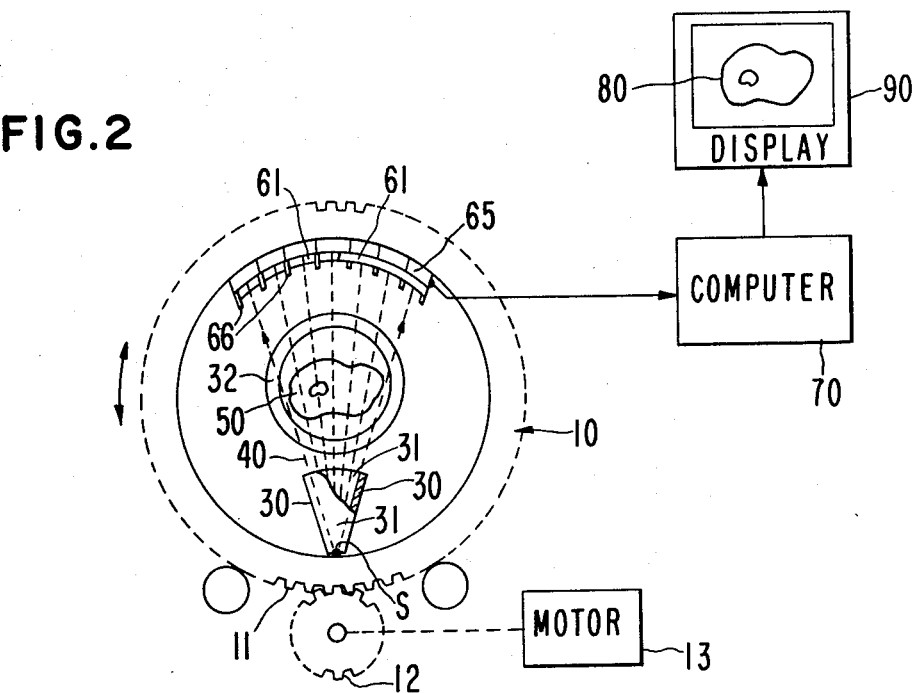
FIG. 2 is a partially schematic, partially block diagram of the embodiment of the instant invention in which the data acquisition phase is discrete.

FIG. 2 is similar to FIG. 1; the only difference is that continuous detector 60 has been replaced by an array or bank of discrete detectors 65, and grid 66 has been added. In cases where the two figures are identical, the description employed above in connection with FIG. 1 applies with equal force to FIG. 2, which illustrates the discrete embodiment of the invention, a special case of the continuous embodiment. The radiation emanating from source S may be a continuous fan or a discrete set of pencil beams (formed, e.g., by a set of collimators) with at least one beam per detector. Discrete detectors 65 typically number 300, although other values may be chosen.

The detector bank is positioned in such a way that the angular distance between detector elements is constant. For example, the bank is arcuate in geometry, or the bank is in a straight line (because easier to build) with each individual detector element aligned with a straight line drawn from the detector element to the source. A grid 66 fabricated of an element such as lead may be associated with each detector element 65 and aligned therewith to minimize the effects of Compton scatter lying in the same quasi-plane as the object slice. This grid is virtually essential when the radiation employed is X-radiation. This grid may optionally be used in the continuous case as well, i.e., where it is anticipated that Compton scatter in the same quasi-plane as the object slice will be a problem. In that application the grid may be made to oscillate or otherwise continuously move with respect to detector 60 so that grid lines do not appear on the output picture.

In the preferred embodiment, a source-detector array is rotated with gantry 10 in a circular path. Periodically (typically, during 360 short moments in time per rotation, on the order of two milliseconds each), radiation is pulsed from the source, absorption values are measured by the detectors 65, are digitalized, smoothed, and fed into a working store within computer 70. Controls are built into the machine so that pulse duration and arcuate angle between pulsing can be quickly adjusted by the operator. These can also be employed in the continuous embodiment where exact data reconstruction is not required.

The data is then processed to yield absorption densities for a preselected plurality of points within object 50 and this reconstructed set of densities is portrayed as output picture 80. The computer may be either hard-wired, firmwared (microprogrammed or PROM-fused), or software programmed (or any combination of the above) to perform the requisite functions, which is true in the continuous embodiment as well.

In one embodiment for use with patients in medical radiology, the apparatus parameters could be as follows:

| | |
|---|---|
| X-ray tube voltage | 120 k V d.c. |
| X-ray tube average current | 250 mA |
| X-ray tube average power | 30 kW |
| X-ray exposure period per object slice | 4 seconds |
| Gantry rotation speed | 0.25 rps |
| Number of X-ray pulses per object slice | 360 |
| Exposure to surface of object | 8 rads |
| X-ray tube pulse current | 1000 mA |
| X-ray pulse duration | 2.8 millisec |
| Interpulse duration | 8.3 millisec |
| Distance from axis to source | 80 cm |
| Distance from source to detector | 160 cm |
| Maximum object slice dimension | 40 cm |
| Fan beam angular spread | 29 degrees |
| Fan beam thickness at middle of object | 8 mm |
| Fan ray interval at middle of object | 1.5 mm |
| Number of fan rays across maximum object slice | 267 |
| Nominal number of detector elements | 300 |
| Fan ray angular interval | 0.109 degrees |
| Source rotation interval per pulse | 1 degree |
| Interval between source pulses at 40 cm diameter object periphery | 3.5 mm |
| X-ray photons per pulse per detector element without object | $2.2 \times 10^8$ |
| Primary photon transmission through 40 cm water | 1/2000 |
| X-ray photons per pulse per detector element through object | $1.1 \times 10^5$ |
| Quantum statistical fluctuation per measurement | 0.33% rms |
| Statistical error in total of 360 measurements through one 1.5 mm × 1.5 mm cell of object slice | 0.6% rms |
| Number of reconstruction points in 40 cm diameter image | 40,000 |
| Spacing between reconstruction points in 40 cm diameter image | 1.8 mm |

If the fan rays were reordered into a new set of parallel rays, bundles of 9 rays extending over successive 1 degree intervals of the fan would be reordered to successive source angular positions 1 degree apart to obtain pseudo-parallel rays. The central rays of these 9-ray bundles would be parallel but their spacing would vary from 1.5 mm to 1.45 mm, an error 3%, depending on whether they came from the center or the edge of the fan beam, due to the source moving on a circle rather than a straight line.

The spacing of individual rays of the fan beam to individual detector elements is 1.5 mm at the middle of the object. The spacing of the central axes of successively pulsed fan beams is 3.5 mm at the periphery of a 40 cm diameter object slice. Better resolution would be obtained for this relatively large size object if 720 pulses at 0.5 degree intervals of gantry rotation were employed, making the spacing of central rays at the object periphery comparable to the spacing of rays within the fan, thereby obtaining more uniform resolution in all directions. The pulse duration would then be 1.4 millisecond and the interpulse duration would be 4.1 millisecond for 4 seconds X-ray exposure per object slice, requiring faster data extraction from the detector elements and twice the number of profile convolution and back-projection computations. Thus, the selection of 360 pulses at 1 degree intervals with a detector of nominal 300 elements represents a practical choice for objects ranging in size from a few cm to 40 cm in diameter.

Let us now examine the method of data reconstruction for both the continuous and discrete cases. Radon's formula for the density at a point P is $$D(P) = -\frac{1}{\pi} \int_0^\infty dr \frac{1}{r} \frac{d\bar{f}(r)}{dr}$$

where r is measured from the point P and f(r) is the average of all line integrals of the density over lines passing a distance r from the point P. J. Radon, Ueber die Bestimmung von Funktionen durch ihre integralwerte laengs gewisser Mannigfaltigkeiten (on the determination of functions from their integrals along certain manifolds), Berichte Saechsische Akadamie der Wissenschaften (Leipzig), Mathematische-Physische Klasse 69, 262-277 (Germany 1917). In this use D(P) represents the extent or density of radiation absorbed at the point P.

Figure 3:
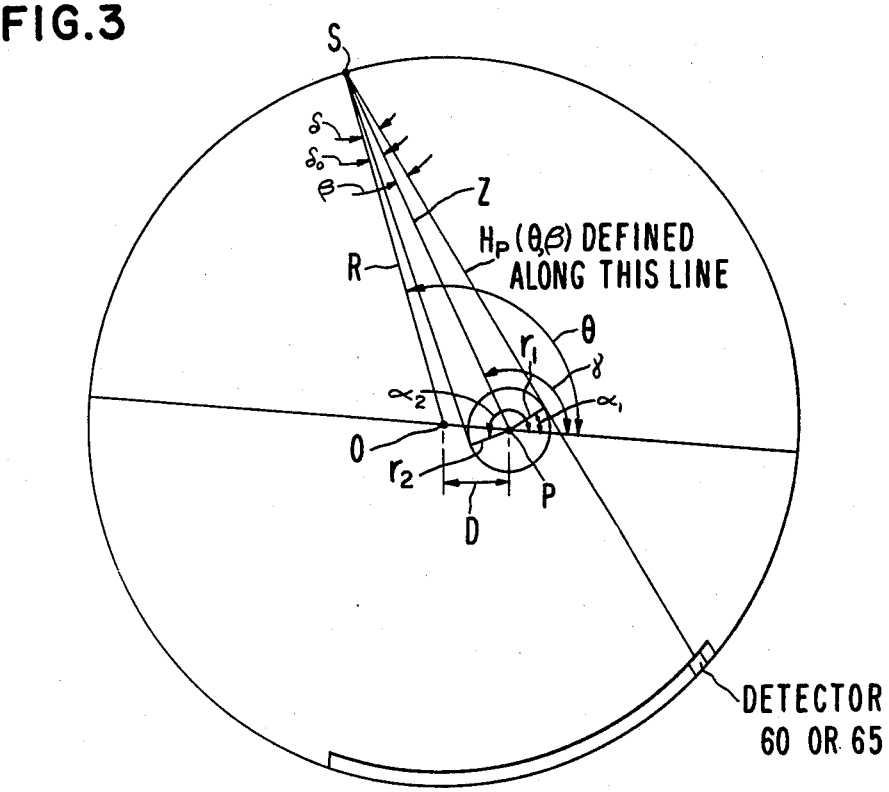
FIG. 3 is a geometrical representation of a preferred method of data acquisition and reconstruction in the instant invention.

Consider the diagram shown in FIG. 3. Define a measurement $H_p(\theta,\beta)$ as the integral (or measurement) of absorbed radiation along a line defined by the angles $\theta$ and $\beta$ and starting at the source point S. In other words, $H=\int Ddx$ where dx is the incremental distance along the cognizant line. The subscript P denotes the fact that $\beta$ is measured from the line drawn from the source S to the point of interest P. If we define I to be the measurement of resulting radiation reaching detector(s) 60 or 65, and $I_o$ to be the radiation which would reach the detector(s) in the absence of any object, such as object 50, which would attenuate any of the radiation as it leaves the source, then we known from basic physical laws that $I=I_o e^{-\int Ddx}=I_o e^{-H}$. In other words, $H=\ln I_o - \ln I = -\ln(I/I_o)$ When the machine is initially calibrated, $I_o$ is chosen so as to be big enough to provide statistically adequate information (e.g., at least $10^3$ X-ray or gamma-ray photons per pulse at each detector element) but not so big as to harm the patient by means of an overdose of radiation in the case where the apparatus is employed for X-ray diagnosis of a patient's body (less than 50 rads of X-ray or gamma-ray dose total for all pulses).

Using Radon's formula we can write $$D(P) = -\frac{1}{\pi} \int_0^\infty dr_1 \frac{1}{r_1} \frac{d}{dr_1} \left\{ \frac{1}{2\pi} \int_0^{2\pi} d\alpha_1 H_p(\theta,\beta) \right\} \quad (3)$$

We must now change the variables of integration from $dr_1 d\alpha_1$ to $d\theta d\beta$. Now $$dr_1 d\alpha_1 = J_1 d\beta d\theta$$

where $J_1$, the Jacobian, is given by $$J_1 = \begin{vmatrix} \frac{\partial r_1}{\partial \beta} & \frac{\partial r_1}{\partial \theta} \\ \frac{\partial \alpha_1}{\partial \beta} & \frac{\partial \alpha_1}{\partial \theta} \end{vmatrix} \quad (4)$$

The coordinates defining the transformation are as follows:

$$r_1 = Z \sin \beta \quad (5)$$

$$\alpha_1 = \beta - \frac{\pi}{2} + \gamma \quad (6)$$

where $$\gamma = \tan^{-1} \frac{R \sin \theta}{R \cos \theta - D} \qquad \begin{matrix} 0 \leq \theta \leq \pi \\ 0 \leq \gamma \leq \pi \end{matrix} \quad (7)$$

$$\gamma = \pi + \tan^{-1} \frac{R \sin \theta}{R \cos \theta - D} \qquad \begin{matrix} \pi \leq \theta \leq 2\pi \\ \pi \leq \gamma \leq 2\pi \end{matrix} \quad (8)$$

when we assume the principal range of $\tan^{-1}$ is 0 to $\pi$.

Evaluating the Jacobian, we find that $$\frac{\partial r_1}{\partial \beta} = Z \cos \beta \quad (9)$$

$$\frac{\partial r_1}{\partial \theta} = \frac{RD \sin \theta}{Z} \sin \beta \quad (10)$$

$$\frac{\partial \alpha_1}{\partial \beta} = 1 \quad (11)$$

$$\frac{\partial \alpha_1}{\partial \theta} = \frac{\partial \gamma}{\partial \theta} = \frac{R^2 - RD \cos \theta}{Z^2} \quad (12)$$

Thus, $$J_1 = \frac{R^2 \cos \beta - RD \cos (\theta - \beta)}{Z} \quad (13)$$

We must also consider the term $$\frac{\partial}{\partial r_1} \{H_p(\theta, \beta)\} = \frac{\partial H_p}{\partial \theta} \frac{\partial \theta}{\partial r_1} + \frac{\partial H_p}{\partial \beta} \frac{\partial \beta}{\partial r_1} \quad (14)$$

The derivatives $$\frac{\partial \theta}{\partial r_1} \text{ and } \frac{\partial \beta}{\partial r_1}$$

can be obtained by implicitly differentiating equations (5) and (6). Consider equation (5). Its derivative is $$1 = \frac{RD \sin \theta \sin \beta}{Z} \frac{\partial \theta}{\partial r_1} + Z \cos \beta \frac{\partial \beta}{\partial r_1} \quad (15)$$

Similarly the derivative of equation (6) with respect to $r_1$ is $$0 = \frac{R^2 - RD \cos \theta}{Z^2} \frac{\partial \theta}{\partial r_1} + \frac{\partial \beta}{\partial r_1} \quad (16)$$

Solving equations (15) and (16) for $$\frac{\partial \theta}{\partial r_1} \text{ and } \frac{\partial \beta}{\partial r_1},$$

we obtain $$\frac{\partial \theta}{\partial r_1} = \frac{Z}{RD \cos (\theta - \beta_1) - R^2 \cos \beta_1} \quad (17)$$

$$\frac{\partial \beta}{\partial r_1} = \frac{RD \cos \theta - R^2}{Z \{RD \cos (\theta - \beta) - R^2 \cos \beta\}} \quad (18)$$

Substituting all these results into equation (3) we finally obtain $$D(P) = -\frac{1}{2\pi^2} \int_0^{2\pi} d\theta \int_0^{\pi} d\beta_1 \frac{1}{Z \sin \beta} \cdot \quad (19)$$

$$\left\{ -\frac{\partial H_p(\theta, \beta_1)}{\partial \theta} + \frac{R^2 - RD \cos \theta}{Z^2} \frac{\partial H_p(\theta, \beta)}{\partial \beta} \right\}$$

Consider the term containing $$\frac{\partial H_p(\theta, \beta)}{\partial \theta}.$$

It can be integrated by parts with respect to $\theta$ to obtain $$\int_0^{2\pi} d\theta \frac{1}{Z} \frac{\partial H_p}{\partial \theta} = \int_0^{2\pi} d\theta \frac{RD \sin \theta}{Z^3} H_p(\theta, \beta) \quad (20)$$

Thus we obtain $$D(P) = -\frac{1}{2\pi^2} \int_0^{2\pi} d\theta \frac{RD \sin \theta}{Z^3} \int_0^{\pi} d\beta \left\{ \frac{-H_p(\theta, \beta)}{\sin \beta} \right\} \quad (21)$$

$$-\frac{1}{2\pi^2} \int_0^{2\pi} d\theta \frac{R^2 - RD \cos \theta}{Z^3} \int_0^{\pi} d\beta \frac{1}{\sin \beta} \frac{\partial H_p(\theta, \beta)}{\partial \beta}$$

In obtaining the above equation it has been assumed that the object does not extend outside the arc covered by the fan beam emanating from the source S. Thus the line integrals of density of rays tangent to circles centered at P such that at least a portion of such circles lie outside the arc covered by the fan beam emanating from the source S are assumed to be zero, where said point of tangency also lies outside said fan beam.

If we again return to FIG. 3 and rewrite Equation (3) using $r_2$ and $\alpha_2$ rather than $r_1$ and $\alpha_1$ we can obtain a second equation for D(P). Thus $$D(P) = -\frac{1}{\pi} \int_0^{\infty} dr_2 \frac{1}{r_2} \frac{\partial}{\partial r_2} \left\{ \frac{1}{2\pi} \int_0^{2\pi} d\alpha_2 H_p(\theta, \beta) \right\} \quad (22)$$

Again we wish to change the variables of integration from $dr_2\, d\alpha_2$ to $d\beta\, d\theta$. Proceeding as before we have $$r_2 = -Z \sin \beta \quad (23)$$

-continued
$$\alpha_2 = \frac{\pi}{2} + \beta + \gamma \quad (24)$$

Evaluating the Jacobian we find $$J_2 = \frac{R^2 \cos\beta - RD\cos(\theta - \beta)}{Z} \quad (25)$$

Evaluating $$\frac{\partial\theta}{\partial r_2} \text{ and } \frac{\partial\beta}{\partial r_2},$$

we obtain $$\frac{\partial\theta}{\partial r_2} = \frac{Z}{R^2\cos\beta - RD\cos(\theta - \beta)} \quad (26)$$

$$\frac{\partial\beta}{\partial r_2} = \frac{R^2 - RD\cos\theta}{Z\{RD\cos(\theta - \beta) - R^2\cos\beta\}} \quad (27)$$

Substituting these expressions into Equation (22), we obtain $$D(P) = +\frac{1}{2\pi^2} \int_0^{2\pi} d\theta \int_{-\pi}^0 d\beta \frac{1}{Z\sin\beta} \cdot \quad (28)$$

$$\left\{ \frac{\partial H_p(\theta,\beta)}{\partial\theta} - \frac{R^2 - RD\cos\theta}{Z^2} \frac{\partial H_p(\theta,\beta)}{\partial\beta} \right\}$$

Again integrating $$\frac{\partial H_p}{\partial\theta}$$

with respect to $\theta$, $$D(P) = +\frac{1}{2\pi^2} \int_0^{2\pi} d\theta \frac{RD\sin\theta}{Z^3} \int_{-\pi}^0 d\beta \frac{H_p(\theta,\beta)}{\sin\beta} - \quad (29)$$

$$\frac{1}{2\pi^2} \int_0^{2\pi} d\theta \frac{R^2 - RD\cos\theta}{Z^3} \int_{-\pi}^0 d\beta \frac{1}{\sin\beta} \frac{\partial H_p}{\partial\beta}$$

Equations (21) and (29) can now be added to obtain $$D(P) = \frac{1}{4\pi^2} \int_0^{2\pi} d\theta \frac{RD\sin\theta}{Z^3} \int_{-\pi}^{+\pi} d\beta \frac{H_p(\theta,\beta)}{\sin\beta} - \quad (30)$$

$$\frac{1}{4\pi^2} \int_0^{2\pi} d\theta \frac{R^2 - RD\cos\theta}{Z^3} \int_{-\pi}^{+\pi} d\beta \frac{1}{\sin\beta} \frac{\partial H_p(\theta,\beta)}{\partial\beta}$$

The following changes can now be made to Equation (30):
(1) Change the variable of integration from $\beta$ to $\delta$ where $\beta = \delta - \delta_o$.
(2) Change $H_p(\theta,\beta)$ to $H_o(\theta,\delta)$ where the subscript o now reflects that $\delta$ is measured from the line connecting the point S and O, the center of rotation.
(3) Note that $$\frac{RD\sin\theta}{Z^3} = \frac{R\sin\delta_o}{Z^2} \quad (31)$$

(4) Note that $$\frac{R^2 - RD\cos\theta}{Z^3} = \frac{R\cos\delta_o}{Z^2} \quad (32)$$

Equation (30) then becomes $$D(P) = \frac{1}{4\pi^2} \int_0^{2\pi} d\theta \frac{R\sin\delta_o}{Z^2} \int_{-\pi}^{+\pi} d\delta \frac{H_o(\theta,\delta)}{\sin(\delta - \delta_o)} - \quad (33)$$

$$\frac{1}{4\pi^2} \int_0^{2\pi} d\theta \frac{R\cos\delta_o}{Z^2} \int_{-\pi}^{+\pi} d\delta \frac{1}{\sin(\delta - \delta_o)} \frac{\partial H_o(\theta,\delta)}{\partial\delta}$$

Equation (33) is the desired result and is the exact solution. It covers the continuous case of data gathering. Although there appears to be a singularity at $\delta = \delta_o$, we are interested in the principal value of the integral. Note that the integral over $\delta$ is in the form of a convolution. Furthermore, if $R \to \infty$, Equation (33) reduces to the simpler parallel geometry case.

Although one could evaluate Equation (33) using analog methods, digital (discrete) techniques are usually employed instead for the following reasons:
(1) With parallel data extraction for fast data acquisition, it is convenient to use a number of discrete detector elements coupled to an equal number of discrete electronic amplifiers.
(2) Because of statistical variations in detected radiation values with finite total radiation exposure and hence finite number of radiation quanta, a point of diminishing returns is reached where dividing the discrete array detector into a larger number of finer elements does not materially improve the quality of the reconstructed image; therefore continuation of this division process to the limit of a continuous detector is not justified.
(3) With continuous rotation of source angular position, the finite fan beam thickness spreads over an equivalent angular spread of the detected data and since there are limits to the accuracy with which this angular spread can be deconvolved, little image quality is lost by exercising the convenience of using a finite number of source position angles.
(4) The presence of the singularity at $\delta = \delta_o$ is not easily handled by analog techniques.
(5) The accuracy required is higher than that normally obtained with analog computation methods.

Equation (33) can be reduced to discrete form as follows. The integrals over $\delta$ cover the full range from from 0 to $2\pi$. Thus we are free to begin and end at any point. Therefore Equation (33) can be written as $$D(P) = \frac{1}{4\pi^2} \int_0^{2\pi} d\theta \frac{R\sin\delta_o}{Z^2} \int_0^{2\pi} d\delta \frac{H_o(\theta,\delta_o + \delta)}{\sin\delta} - \quad (35)$$

$$\frac{1}{4\pi^2} \int_0^{2\pi} d\theta \frac{R\cos\delta_o}{Z^2} \int_0^{2\pi} d\delta \frac{1}{\sin\delta} \frac{\partial H_o(\theta,\delta_o + \delta)}{\partial\delta}$$

Now let $\Delta$ be the angular distance between measurements and further let $$\Delta = \frac{2\pi}{4N}.$$

Then $H_o(\theta, \delta_o + \delta)$ can be expanded in a finite Fourier series as follows:

$$H_o(\theta, \delta_o + \delta) = \frac{a_o(\theta, \delta_o)}{2} + \sum_{n=1}^{2N-1} a_n(\theta, \delta_o)\cos(n\delta) + \sum_{n=1}^{2N-1} b_n(\theta, \delta_o)\sin(n\delta) + \frac{a_{2N}(\theta, \delta_o)}{2} \cos(2N\delta) \qquad (36)$$

Since $$\int_{-\pi}^{+\pi} \frac{\sin nx}{\sin x} dx = \begin{cases} 2\pi & n \text{ ODD} \\ 0 & \text{OTHERWISE} \end{cases} \qquad (37)$$

and $$\int_{-\pi}^{+\pi} \frac{\cos nx}{\sin x} dx = 0 \qquad (38)$$

Equation (35) can be written as:

$$D(P) = -\frac{1}{2\pi} \int_0^{2\pi} d\theta \frac{R\sin\delta_o}{Z^2} S_b(\theta, \delta_o) + \frac{1}{2\pi} \int_0^{2\pi} d\theta \frac{R\cos\delta_o}{Z^2} S_a(\theta, \delta_o) \qquad (39)$$

where $$S_a(\theta, \delta_o) = \sum_{\substack{n=1 \\ \&\text{ODD}}}^{2N-1} n a_n(\theta, \delta_o) \qquad (40)$$

$$S_b(\theta, \delta_o) = \sum_{\substack{n=1 \\ \&\text{ODD}}}^{2N-1} b_n(\theta, \delta_o) \qquad (41)$$

Now $$a_n(\theta, \delta_o) = \frac{1}{2N} \sum_{m=0}^{4N-1} H_o(\theta, \delta_o + m\Delta)\cos(mn\Delta) \qquad (42)$$

$$b_n(\theta, \delta_o) = \frac{1}{2N} \sum_{m=0}^{4N-1} H_o(\theta, \delta_o + m\Delta)\sin(mn\Delta) \qquad (43)$$

Therefore $$S_a(\theta, \delta_o) = \frac{1}{2N} \sum_{m=0}^{4N-1} H_o(\theta, \delta_o + m\Delta) \sum_{\substack{n=1 \\ \&\text{ODD}}}^{2N-1} n\cos(nm\Delta) \qquad (44)$$

$$S_b(\theta, \delta_o) = \frac{1}{2N} \sum_{m=0}^{4N-1} H_o(\theta, \delta_o + m\Delta) \sum_{\substack{n=1 \\ \&\text{ODD}}}^{2N-1} \sin(nm\Delta) \qquad (45)$$

The summations over $\eta$ can be evaluated $$\sum_{\substack{n=1 \\ \&\text{ODD}}}^{2N-1} n\cos(nm\Delta) = \frac{d}{d(m\Delta)}\left(\frac{\sin^2(Nm\Delta 1)}{\sin(m\Delta)}\right) = \qquad (46)$$

$$\begin{cases} N^2 & m = 0 \\ -\frac{\cos(m\Delta)}{\sin^2(m\Delta)} & m \text{ ODD} \quad \Delta = \frac{2\pi}{4N} \\ 0 & m \text{ EVEN} \end{cases}$$

and $$\sum_{\substack{n=1 \\ \&\text{ODD}}}^{2N-1} \sin(nm\Delta) = \frac{\sin^2(Nm\Delta)}{\sin(m\Delta)} = \qquad (47)$$

$$\begin{cases} 0 & m \text{ EVEN} \\ \frac{1}{\sin(m\Delta)} & m \text{ ODD} \quad \Delta = \frac{2\pi}{4N} \end{cases}$$

If we now replace N by $$\left(\frac{\pi}{2\Delta}\right),$$

then we can write $$S_a(\theta, \delta_o) = \left(\frac{\pi}{4\Delta}\right) H_o(\theta, \delta_o) - \left(\frac{\Delta}{\pi}\right) \sum_{m \text{ ODD}} \frac{\cos(m\Delta)}{\sin^2(m\Delta)} H_o(\theta, \delta_o + m\Delta) \qquad (48)$$

and $$S_b(\theta, \delta_o) = \left(\frac{\Delta}{\pi}\right) \sum_{m \text{ ODD}} \frac{1}{\sin(m\Delta)} H_o(\theta, \delta_o + m\Delta) \qquad (49)$$

If we now substitute Equations (48) and (49) into Equation (39) and replace the integration over $\theta$ by a summation, we obtain:

$$D(P) = \sum_\theta d\theta \left\{ \frac{R\sin\delta_o}{Z^2}\left[\left(\frac{\Delta}{2\pi^2}\right) \sum_{m \text{ ODD}} \frac{1}{\sin(m\Delta)} H_o(\theta, \delta_o + m\Delta)\right] + \frac{R\cos\delta_o}{Z^2}\left[\frac{1}{8\Delta} H_o(\theta, \delta_o) - \left(\frac{\Delta}{2\pi^2}\right) \sum_{m \text{ ODD}} \frac{\cos(m\Delta)}{\sin^2(m\Delta)} H_o(\theta, \delta_o + m\Delta)\right]\right\} \qquad (50)$$

This again can be simplified to $$D(P) = \sum_\theta d\theta \frac{R}{Z^2}\left\{\frac{H_o(\theta, \delta_o)\cos\delta_o}{8\Delta} - \frac{\Delta}{2\pi^2} \sum_{m \text{ ODD}} \frac{\cos(\delta_o + m\Delta)H_o(\theta, \delta_o + m\Delta)}{\sin^2(m\Delta)}\right\} \qquad (51)$$

In both Equations (50) and (51), the limits on the summation over m have not been written. This summation is taken over all detectors; m can be both positive or negative and is simply the number of detectors away from the detector at $\delta_o$.

The expression within brackets in Equation (51), which must be evaluated first, represents a convolution and the remaining portion of Equation (51), represents a back-projection. The slow way to evaluate Equation (51) would be to calculate the absorption density at each point P for each of the values detected, but there are faster ways of solving Equation (51) for many values of P at once. Typically P's are about 40,000 in number, representing a 200×200 grid superimposed over object 50. The points P may be uniformly spaced or non-uniformly spaced. When 360 values were chosen for $\theta$ and 300 detectors were selected, the data collection was performed in about 6 seconds. This is between one and two orders of magnitude faster than the existing prior art for the same quality picture. One sees that as $\Delta$ decreases and the numbers of measurements, $\theta$'s, and P's increase, a more accurate picture may be obtained but at a cost of greater data collection and reduction times.

As stated before, the $H_o(\theta,\delta_o+m\Delta)$'s are obtained as a result of measurements taken at detector elements 65. The index m is measured from $\delta_o$, i.e., the location of the line through the point of interest P running from source S to the detector elements. In other words $H_o(\theta,\delta_o)$ represents that detector element along the straight line running from S through P; $H_o(\theta,\delta_o+\Delta)$, $H_o(\theta,\delta_o+2\Delta)$, etc. represent the detector elements running sequentially in one direction from $\delta_o$; and $H_o(\theta,\delta_o-\Delta)$, $H_o(\theta, \delta_o-2\Delta)$, etc., the detector elements running sequentially in the opposite direction. The data from the detectors may be extracted serially or in parallel.

For each value of $\theta$ and for each value of $\delta_o$, a single convolution profile value is calculated and stored in a storage device or array $C(\theta,\delta_o)$. This calculation for all $\delta_o$'s for each $\theta$ may be performed as soon as the data-gathering phase for that particular $\theta$ is complete, i.e., while the source continues to rotate about its path. The outer loop (the back-projection portion) of Equation (51) may also be completed for each $\theta$ as soon as all measurements for that particular $\theta$ have been read into storage and the inner loop (convolution) is complete. Thus, measurements and calculations are performed simultaneously; this is one, but by no means the most important, way the technique of the present invention saves time.

At the time of the back-projection loop, interpolations are performed to take into account the fact that most of the P's do not lie along a line running from the source S to the mid-point of a detector element. It is sufficient but not necessary that the interpolations be linear. The convolution profile values utilized in the linear interpolation are those associated with the mid-points (or other normal detection points) of those detector elements adjacent to the point along the detector array cut by the straight line running from the source S through the point P in question. This interpolation could also be performed during the convolution step.

After all calculations have been performed, the values of absorption densities at each point P may then be portrayed in graphic form as output picture 80.

Figure 4:
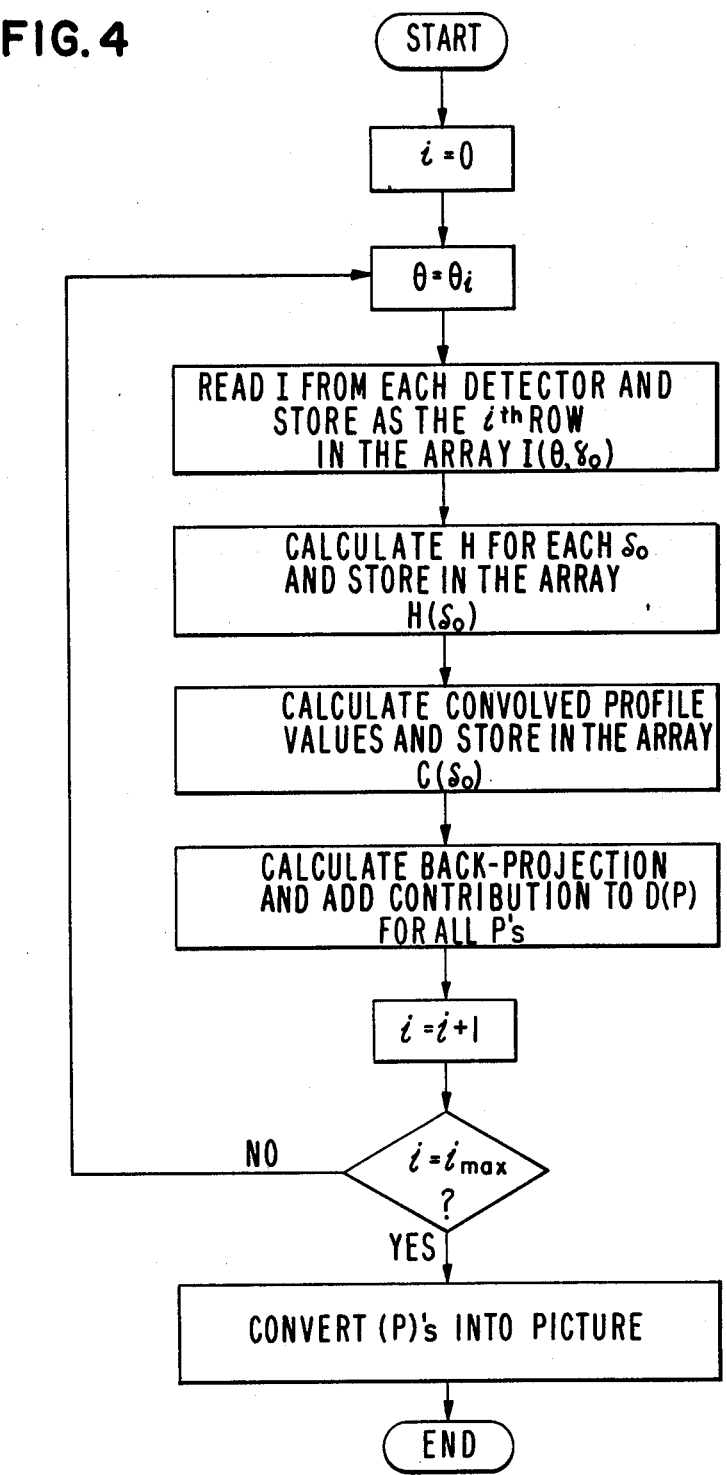
FIG. 4 is a flow diagram which illustrates a typical embodiment of data acquisition and reconstruction in the discrete embodiment of the instant invention.

A greater insight into how an output picture is produced may be obtained by studying FIG. 4. The index for $\theta$ is i and is initialized to zero. At $\theta_i$ radiation passes through the object and is read by the detector elements as values of I. At this point the source is free to rotate to its next value of $\theta$; this in fact would be done if the main criterion were to minimize the data gathering time, or if two processors existed within the computer, one for data gathering and one for data reduction. In the latter case, much of the data reduction could be performed simultaneously with the data collection. However (for purposes of discussion but without intending to limit in any way the invention), the flow chart shows a data-reconstruction embodiment in which calculations are performed at this time, before the source rotates to its next value of $\theta$. In the case of administering X-radiation to humans, this does not result in extra radiation entering the body, because the radiation is normally pulsed for just a short time for each value of $\theta$. Next, H is calculated at each detector element and stored in the storage area or array $H(\theta,\delta_o)$. At this point, the source may rotate to its next value of $\theta$, and the same considerations govern as to the desirability of so doing. For $\theta_i$ and each value of $\delta_o$ the convolution profile value is obtained and stored in a second storage area or array $C(\theta,\delta_o)$. Again at this point the source may rotate to its next value of $\theta$; however, the flow diagram illustrates the case where an additional step is performed at this time.

It will readily be seen that many permutations of the steps are possible. The important point is that for each set of measurements taken for a particular $\theta$, either the convolution step or the convolution step plus the back projection step may be performed at that time, with or without subsequent rotation and measurement gathering for additional values of $\theta$. Unless the processor is extremely fast, if the same processor is both reading the data and performing the convolution and back-projecting steps, then normally all of the data will first be read so as to minimize the data collection time. If, on the other hand, an additional processor is employed for just the data gathering step, then much time can be saved by providing for simultaneous performance of the convolution and back-projection steps.

Notice that for each P, Z is unique and may be preobtained; Z may also be thought of as a function of $\theta$ and $\delta$ or $\theta$ and m. During the outer loop (the back projection portion), a correction is performed by means of linear or other interpolation to take into account the fact that the line running from the source S through the point P will not normally strike a detector element at its midpoint (or other point in the detector element where the measurement is normally taken).

In other words, if the cognizant line strikes the detector bank 1/10 of the distance between the detection points of detector elements $m_1$ and $m_2$, then it is assumed for the purposes of the calculation that the equivalent value of C for this line is 9/10 the C based on $m_1+1/10$ the C based at $m_2$.

Returning to FIG. 4, the index i is then incremented. The question is asked, "Does i equal the maximum value preselected?" (A typical value for $i_{max}$ is 360). If not, then the value of $\theta$ is incremented accordingly and a new series of measurements or measurements plus calculations is performed. If i equals $i_{max}$, then we know that we are done with the data collection and pre-calculation portions of the process and all that remains is to complete the calculations and convert the D(P)'s into picture form. In the case illustrated by FIG. 4, all that remains is, for each value of P, to convert the D(P)'s into picture form for visual inspection by the observer.

Much of the above discussion, which pertains to the discrete embodiment, also applies to the continuous embodiment, i.e., the graphic portrayal of equation (33).

While the principles of the invention have now been made clear in the illustrated embodiment shown above, there will be obvious to those reasonably skilled in the art many modifications in arrangement of components and choices of variables used in the practice of the invention without departing from the above enunciated principles.

For example, other convolution functions than the one detailed herein may be employed. Further, it must be remembered that the technique of the invention can be employed over a wide range of applications, such as transmissive ultrasonics, electron microscopy, and others, as long as radiation in the shape of a fan beam can be caused to pass through an object at a plurality of angles and then detected.

The appended claims are intended to cover and embrace any such modification within the limits only of the true spirit and scope of the invention.

What is claimed is:

1. Apparatus for examining an object with radiation, said apparatus comprising:

support means mounted for rotation about a fixed axis;

source means forming a fan shaped planar beam of radiation, said source means being mounted on said support means with said beam directed toward said axis;

detector means for detecting said fan beam, said detector means being mounted on said support means and positioned on the side of said axis of rotation opposite from said source means; and said source means and detector means being rigidly attached to said support means during operation; whereby in operation of said apparatus said support means, source means and detector means are all constrained against motion in any direction except rotation about said fixed axis;

means for continuously rotating said support means;

means for turning said beam on and off periodically during said continuous rotation;

means for performing a non-reordering convolution operation on signals derived from the fan beam received by said detector means at positions of the fan beam, thus arranging said signal in convolved form representative of radiation absorbed by said object at each of said positions; and display means responsive to said means for performing a non-reordering convolution operation for providing a visual portrayal of radiation absorbed by said object.

* * * * *